US008513258B2

(12) United States Patent
Perez et al.

(10) Patent No.: US 8,513,258 B2
(45) Date of Patent: Aug. 20, 2013

(54) CINNAMOYL-PIPERAZINE DERIVATIVES AND THEIR USE AS PAR-1 ANTAGONISTS

(75) Inventors: Michel Perez, Castres (FR); Marie Lamothe, Castres (FR); Bruno Le Grand, Lautrec (FR); Robert Letienne, Castres (FR)

(73) Assignee: Pierre Fabre Medicament, Boulogne-Billancourt (FR)

(*) Notice: Subject to any disclaimer, the term of this patent is extended or adjusted under 35 U.S.C. 154(b) by 0 days.

(21) Appl. No.: 13/476,487

(22) Filed: May 21, 2012

(65) Prior Publication Data

US 2012/0232097 A1 Sep. 13, 2012

Related U.S. Application Data

(62) Division of application No. 12/305,584, filed as application No. PCT/EP2007/056086 on Jun. 19, 2007, now Pat. No. 8,217,046.

(30) Foreign Application Priority Data

Jun. 19, 2006 (FR) ..................................... 06 05419

(51) Int. Cl.
*A61K 31/495* (2006.01)
*C07D 295/185* (2006.01)

(52) U.S. Cl.
USPC ...................................... 514/255.01; 544/391

(58) Field of Classification Search
None
See application file for complete search history.

(56) References Cited

U.S. PATENT DOCUMENTS 6,207,665 B1   3/2001   Bauman et al.

FOREIGN PATENT DOCUMENTS

WO    WO 02/076965 A1    10/2002
WO    WO 2008/155335 A1   12/2008

OTHER PUBLICATIONS

Ahn et al., "Nonpeptide thrombin receptor antagonists", Drug of the Future, vol. 26, No. 11, pp. 1065-1085, 2001.
Algermissen et al., "Distribution and potential biologic function of the thrombin receptor PAR-1 on human keratinocytes", Arch. Dermatol. Res., vol. 292, pp. 488-495, 2000.
Arunlakshana et al., "Some quantitative uses of drug antagonists", Brit. J. Pharmacol., vol. 14, pp. 48-58, 1959.
Boire et al., "PAR1 is a matrix metalloprotease-1 receptor that promotes invasion and tumorigenesis of breast cancer cells", Cell, vol. 120, pp. 303-313, 2005.
Coughlin et al., "Characterization of a functional thrombin receptor", J. Clin. Invest., vol. 89, No. 2, pp. 351-355, 1992.
Derian et al., "Blockage of the thrombin receptor protease-activated receptor-1 with a small-molecule antagonist prevents thrombus formation and vascular occlusion in nonhuman primates", Journal of Pharmacology and Experimental Therapeutics, vol. 304, No. 2, pp. 855-861, 2003.
Even-Ram et al., "Thrombin receptor overexpression in malignant and physiological invasion processes", Nature Medicine, vol. 4, No. 8, pp. 909-914, 1998.
Fiorucci et al., "PAR1 antagonism protects against experimental liver fibrosis. Role of proteinase receptors in stellate cell activation", Hepatology, vol. 39, pp. 365-375, 2004.
Hamilton et al., "Heterogeneous mechanisms of endothelium-dependent relaxation for thrombin and peptide activators of protease-activated receptor-1 in porcine isolated coronary artery", British Journal of Pharmacology, vol. 130, pp. 181-188, 2000.
Hung et al., "Thrombin-Induced Events in Non-Platelet Cells Are mediated by the Unique Proteolytic Mechanism Established for the Cloned Platelet Thrombin Receptor", J. Cell. Biol., vol. 116, No. 3, pp. 827-832, 1992.
Maryanoff et al., "Discovery of potent peptide-mimetic antagonists for the human thrombin receptor, protease-activated receptor-1 (PAR-1)", Curr. Med. Chem., Cardiovascular & Hematological Agents, vol. 1, pp. 13-36, 2003.
Meyer-Hoffert et al., "Trypsin induces epidermal proliferation and inflammation in murine skin", Experimental Dermatology, vol. 13, pp. 234-241, 2004.
Moffatt et al., "Shooting for PARs in lung diseases", Current Opinion in Pharmacology vol. 4, pp. 221-229, 2004.
O'Brien et al., "Thrombin responses in human endothelial cells", J. Biol. Chem., vol. 275, No. 18, pp. 13502-13509, 2000.
Ossovskaya et al., "Protease-activated receptors: contribution to physiology and disease", Physiol. Rev., vol. 84, pp. 579-621, 2004.
Schechter et al., "Reaction of mast cell protease tryptase and chymase with protease activated receptors (PARs) on keratinocytes and fibroblasts", Journal of Cellular Physiology, vol. 176, pp. 365-373, 1998.
Steinberg, Susan F., "The cardiovascular actions of protease-activated receptors", Molecular Pharmacology, vol. 67, No. 1, pp. 2-11, 2005.
Vergnolle et al., "A role for proteinase-activated receptor-1 in inflammatory bowel diseases", Journal of Clinical Investigation, vol. 114, No. 10, pp. 1444-1456, 2004.

(Continued)

*Primary Examiner* — Emily Bernhardt
(74) *Attorney, Agent, or Firm* — Birch, Stewart, Kolasch & Birch, LLP

(57) ABSTRACT

The present invention relates to compounds of general formula (I):

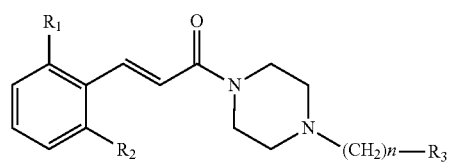

wherein:
$R_1$ represents:
  halogen, CN or $NO_2$;
$R_2$ represents:
  hydrogen or halogen;
n represents:
  1 or 2;
$R_3$ represents:
  phenyl substituted by one or more halogens or $C_1$-$C_6$ alkyls; or a cyclohexyl;
as well as the therapeutically-acceptable salts or solvates thereof.
These compounds are useful as protease-activated receptor-1 (PAR-1) antagonists, particularly in the treatment of thrombosis.

4 Claims, No Drawings

(56) References Cited

OTHER PUBLICATIONS

Vippagunta et al Advanced Drug Delivery Reviews, vol. 48, pp. 3-26 (2001).
Vu et al., "Domains specifying thrombin-receptor interaction", Nature, vol. 353, pp. 674-677, 1991.
Vu et al., "Molecular cloning of a functional thrombin receptor reveals a novel proteolytic mechanism of receptor activation", Cell, vol. 64, pp. 1057-1068, 1991.

CINNAMOYL-PIPERAZINE DERIVATIVES AND THEIR USE AS PAR-1 ANTAGONISTS

The present application is a 37 C.F.R. §1.53(b) divisional of, and claims priority to, U.S. application Ser. No. 12/305,584, filed Dec. 18, 2008 now U.S. Pat. No. 8,217,046. Application Ser. No. 12/305,584 is the national phase under 35 U.S.C. §371 of International Application No. PCT/EP2007/56086, filed on Jun. 19, 2007. Priority is also claimed to French Application No. 0605419 filed on Jun. 19, 2006. The entire contents of each of these applications is hereby incorporated by reference.

The present invention relates to cinnamoyl-piperazine derivatives, a method of manufacturing same, pharmaceutical compositions comprised of same and the use of same as drugs for the treatment and/or prevention of arterial and/or venous thrombosis, acute coronary syndromes, restenosis, stable angina, heart rhythm disorders, myocardial infarction, hypertension, heart failure, stroke, inflammatory disorders, pulmonary diseases, gastrointestinal diseases, fibrosis development in chronic liver disease patients, cancer and skin diseases. The present invention also relates to combinations of the inventive compounds with other cardiovascular agents.

Thrombosis is regarded as a primary factor in vascular occlusion, which is the cause of a number of pathophysiological complications. Antithrombotic therapy is thus extremely important as it can reduce the risk of cardiovascular mortality and coronary events. Although several types of molecules have shown effective antithrombotic activity in man, a need for novel molecules remains. Indeed, improvements can be made to existing compounds, some of which have a negative impact on bleeding time or are accompanied by other undesirable side effects (such as, for example, the risk of ulcer with aspirin).

Protease-activated receptor-1 (PAR-1) was recently cloned (Vu et al., Cell, 1991, 64: 1057-1068) and its mechanism of action elucidated (Coughlin et al., J. Clin. Invest. 1992, 89(2): 351-355). This receptor, notably present on the surface of platelets but also on the surface of endothelial cells (O'Brien et al., J. Biol. Chem. 2000, 275: 13502-13509), smooth muscle cells (Hamilton et al., Br. J. Pharmacol. 2000, 130: 181-188) and fibroblasts (Hung et al., J. Cell. Biol. 1992, 116(3): 827-832), is activated by thrombin and thus is also called thrombin receptor. The N-terminus of the protein is cleaved by thrombin between arginine 41 and serine 42 to free a new end which will act, after folding upon the active site, as a receptor agonist (Vu et al., Nature, 1991, 353, 674-677). With respect to platelets, this specific PAR-1 receptor activation mechanism leads to thrombin-mediated platelet aggregation.

The blocking of this activation, for example with PAR-1 receptor antagonists, can inhibit thrombin-mediated platelet aggregation (Ahn et al., Drug of the Future, 2001, 26: 1065-1085). The blocking of these receptors can thus lead to the treatment or prevention of thrombosis (Derian et al., J. Pharmacol. Exp. Ther., 2003, 855-861), acute coronary syndromes (Ossovskaya et al., Physiol. Rev., 2004, 84: 579-621) and restenosis (Maryanoff et al., Curr. Med. Chem. Cardiovasc. Hematol. Agents., 2003, 13-36) and can reduce myocardial necroses during infarction or reperfusion (Steinberg et al., Mol. Pharmacol. 2005, 67: 2-11). PAR-1 antagonist activity can prevent certain inflammatory diseases in the pulmonary system (Moffatt et al., Curr. Op. Pharmacol., 2004, 221-229) and in the gastrointestinal system (Vergnolle et al., J. Clin. Invest., 2004, 1444-1456). PAR-1 antagonists can also be of use in the treatment of fibroses in patients with chronic liver disease (Fiorucci et al., Hepatology, 2004, 39: 365-375). They can also be of use as anti-cancer agents given that they act to control cellular proliferation and metastases (Evan-Ram et al., Nat. Med., 1998, 909-914; Boire et al., Cell., 2005, 120: 303-313). Lastly, PAR-1 antagonists can be of interest in dermatology to treat certain skin diseases (Schechter et al., J. Cell. Physiol., 1998, 176:365-373; Algermissen et al., Arch. Dermatol. Res., 2000, 292:488-495; Meyer-Hoffert et al., Exp. Dermatol., 2004, 13: 234-241).

The present invention relates to a novel class of PAR-1 antagonists that are distinguished from the prior art by their different chemical structure and their remarkable biological property.

Compounds of the present invention are of general formula (I):

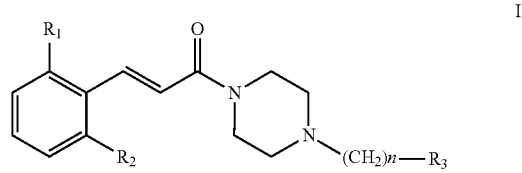

wherein:
$R_1$ represents:
   halogen, CN or $NO_2$;
$R_2$ represents:
   hydrogen or halogen;
n represents:
   1 or 2;
$R_3$ represents:
   phenyl substituted by one or more halogens or $C_1$-$C_6$ alkyls; or a cyclohexyl;
or the therapeutically-acceptable salts or solvates thereof.

In the preceding definitions:

All combinations of substituents or variables are possible insofar as they lead to stable compounds.

The term "halogen" represents fluorine, chlorine, bromine or iodine.

The term "alkyl" represents linear or branched, saturated or unsaturated aliphatic hydrocarbon chains comprising the specified number of carbon atoms.

Therapeutically-acceptable salts of compounds of the present invention include conventional nontoxic salts of compounds of the invention such as those formed from organic or inorganic acids. As an example, the following can be cited: inorganic acid salts such as hydrochloric, hydrobromic, phosphoric and sulfuric acids, as well as organic acid salts such as acetic, trifluoroacetic, propionic, succinic, fumaric, malic, tartaric, citric, ascorbic, maleic, glutamic, benzoic, salicylic, toluenesulfonic, methanesulfonic, stearic and lactic acids.

These salts can be synthesized from compounds of the invention containing a base moiety and corresponding acids according to conventional chemical methods.

Therapeutically-acceptable solvates of compounds of the present invention include conventional solvates such as those formed during the final preparation step of compounds of the invention as a result of the presence of solvents. Solvates due to the presence of water or ethanol can be cited as an example.

Among the compounds of general formula (I) according to the present invention, one particularly advantageous class of compounds are compounds of general formula (I) wherein $R_1$ is halogen, $R_2$ is hydrogen, n equals 1 and $R_3$ is phenyl substituted by one or more halogens or $C_1$-$C_6$ alkyls.

Another particularly advantageous class of compounds according to the present invention is compounds of general formula (I) wherein $R_1$ is cyano, $R_2$ is hydrogen, n equals 1 and $R_3$ is phenyl substituted by one or more halogens or $C_1$-$C_6$ alkyls.

Another particularly advantageous class of compounds according to the present invention is compounds of general formula (I) wherein $R_1$ is halogen, $R_2$ is hydrogen, n equals 1 and $R_3$ is cyclohexyl.

Another particularly advantageous class of compounds according to the present invention is compounds of general formula (I) wherein $R_1$ is cyano, $R_2$ is hydrogen, n equals 1 and $R_3$ is cyclohexyl.

The present invention also relates to the preparation of compounds of general formula (I) by the general methods described in the following synthesis diagrams supplemented by, as the case may be, any standard technique described in the literature, known to those persons skilled in the art, or presented in the experiments section.

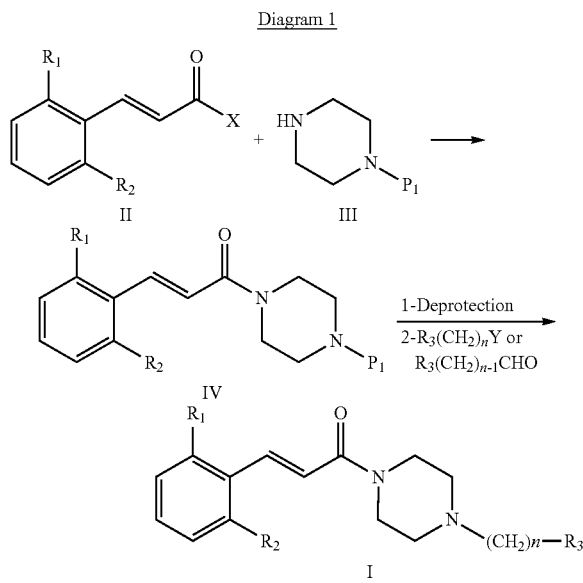

Diagram 1

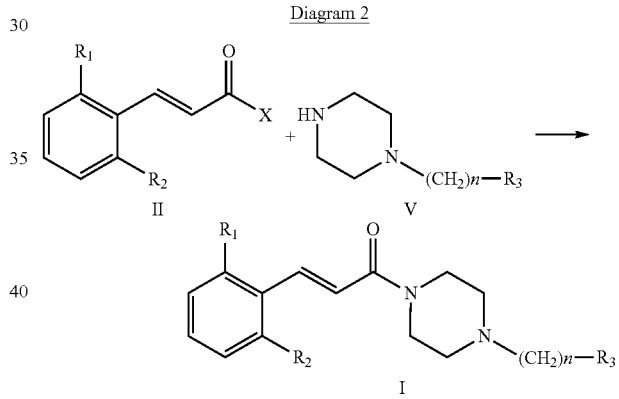

Diagram 2

Diagram 1 illustrates the first general method that can be used for the preparation of compounds of general formula (I). In the general formulas above, $R_1$, $R_2$, $R_3$ and n are defined as in the preceding description of general formula (I). $P_1$ represents a protective group. X can represent a leaving group such as chlorine. In this case, the first step consists of the reaction between an acid chloride and an amine. This reaction can be carried out by methods and techniques known to those persons skilled in the art. A particularly advantageous method consists of reacting the two entities in the presence of an organic or inorganic base such as, for example, $Et_3N$, $iPr_2NEt$, pyridine, NaH, $Cs_2CO_3$ or $K_2CO_3$ in a solvent such as THF, dichloromethane, DMF or DMSO at a temperature between −20° and 100° C. X can also represent hydroxyl. In this case, the first step is a condensation reaction between the carboxylic acid (II) and the amine (III). This reaction can be carried out by methods and techniques known to those persons skilled in the art. A particularly advantageous method consists of reacting these two entities in the presence of 1-(3-dimethylaminopropyl)-3-ethyl-carbodiimide (EDC), 3-hydroxy-1,2,3-benzotriazin-4(3H)-one, and a tertiary amine such as diisopropylethylamine in a polar aprotic solvent, such as dichloromethane or DMF, at a temperature between −15° C. and 40° C.

After deprotection of the intermediate (IV) by methods and techniques known to those skilled in the art ("Protective Groups in Organic Synthesis," T. W. Greene, John Wiley & Sons, 1981 and "Protecting Groups," P. J. Kocienski, Thieme Verlag, 1994), the intermediate obtained can react with a reagent of formula $R_3(CH_2)_nY$, wherein Y represents a leaving group such as, for example, Cl, Br, I, $OSO_2CH_3$, $OSO_2CF_3$ or O-tosyl. In this case, the reaction will be carried out in the presence of an organic or inorganic base such as, for example, $Et_3N$, $iPr_2NEt$, NaH, $Cs_2CO_3$ or $K_2CO_3$ capable of being supported on a resin such as PS-DIEA or MP-carbonate, in a polar anhydrous solvent such as dichloromethane, THF, DMF or DMSO at a temperature between −20° and 100° C. Another preparation method consists of carrying out a reducing amination reaction using an aldehyde of formula $R_3$—$(CH_2)_{n-1}$—CHO in which $R_3$ and n are as defined previously, with the deprotected amine of general formula (IV) and a reducing agent such as $NaBH_4$, $NaBH_3CN$ or $NaBH(OAc)_3$ capable of being supported on a resin such as $MP-BH_3CN$, in a polar solvent such as 1,2-dichloroethane, dichloromethane, THF, DMF or MeOH, at a pH that can be controlled by the addition of an acid such as acetic acid, at a temperature between −20° C. and 100° C.

Diagram 2 illustrates the second general method that can be used for the preparation of compounds of general formula (I). In the general formulas above, $R_1$, $R_2$, $R_3$ and n are defined as in the preceding description of general formula (I). X can represent a leaving group such as chlorine. In this case, synthesis consists of the reaction between an acid chloride and an amine. This reaction can be carried out by methods and techniques known to those persons skilled in the art. A particularly advantageous method consists of reacting the two entities in the presence of an organic or inorganic base such as, for example, $Et_3N$, $iPr_2NEt$, pyridine, NaH, $Cs_2CO_3$ or $K_2CO_3$ in a solvent such as THF, dichloromethane, DMF or DMSO at a temperature between −20° and 100° C.

X can also represent hydroxyl. In this case, synthesis consists of condensation between the carboxylic acid (II) and the amine (V). The reaction can be carried out by methods and techniques known to those persons skilled in the art. A particularly advantageous method consists of condensing a carboxylic acid of general formula (II) with an amine of general formula (V) in the presence of 1-(3-dimethylaminopropyl)-3-ethyl-carbodiimide (EDC), 3-hydroxy-1,2,3-benzotriazin-4(3H)-one and a tertiary amine such as diisopropylethylamine, in a polar aprotic solvent such as dichloromethane, at a temperature between −15° C. and 40° C.

When it is desired to isolate a compound of general formula (I) containing at least one base function in salt state by the addition of an acid, such a result can be achieved by treating the free base of general formula (I) (in which at least one base function is present) with a suitable acid, preferably in an equivalent quantity.

The examples which follow illustrate the invention without limiting its scope in any way.

EXAMPLE 1

3-(2-Chloro-phenyl)-1-[4-(4-fluoro-benzyl)-piperazin-1-yl]-propenone

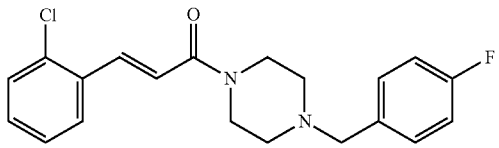 [SMILES: O=C(/C=C/c1ccccc1Cl)N1CCN(Cc2ccc(F)cc2)CC1]

EXAMPLE 1A 4-(4-Fluoro-benzyl)-piperazine-1-carboxylic acid tert-butyl ester

Piperazine-1-carboxylic acid tert-butyl ester (5.0 g, 26.8 mmol) in solution in dichloromethane (100 ml) in the presence of diisopropylethylamine (DIEA) (5.59 ml, 40.2 mmol) is treated with 4-fluorobenzyl bromide (3.68 ml, 29.5 mmol) at room temperature. After 16 hours of agitation the reaction mixture is diluted with dichloromethane and washed with water. The organic phase is dried on $MgSO_4$, filtered and evaporated to dryness. The syrup obtained is purified by silica column chromatography and eluted with a 98/2 to 95/5 $CH_2Cl_2$/MeOH mixture. Product 1A is isolated in the form of a white solid (7.03 g, 88%).

$^1$H NMR, DMSO-$d_6$ (ppm): 1.38 (s, 9H); 2.29 (t, 4H); 3.30 (broad s, 4H); 3.45 (s, 2H); 7.14 (t, 2H); 7.32 (dd, 2H).

EXAMPLE 1B

-4-(4-Fluoro-benzyl)-piperazine 4-(4-Fluoro-benzyl)-piperazine-1-carboxylic acid tert-butyl ester (7.03 g, 23.8 mmol) in solution in toluene (300 ml) is treated with trifluoroacetic acid (53.2 ml, 716 mmol) at room temperature. After 2 hours of agitation the reaction mixture is diluted with dichloromethane, washed with 1 N soda and then with water. The organic phase is dried on $MgSO_4$, filtered and evaporated to dryness. The crude product is isolated for the following reaction (4.2 g, 90%).

EXAMPLE 1

-3-(2-Chloro-phenyl)-1-[4-(4-fluoro-benzyl)-piperazin-1-yl]-propenone

A mixture of 2-chloro-cinnamic acid (2.43 g, 13.3 mmol) and 4-(4-fluoro-benzyl)-piperazine (2.16 g, 11.1 mmol) in solution in dichloromethane (70 ml) is treated with 1-(3-dimethylaminopropyl)-3-ethylcarbodiimide (EDCI) hydrochloride (2.55 g, 13.3 mmol) and 3-hydroxy-1,2,3-benzotriazin-4(3H)-one (HOOBT) (2.17 g, 13.3 mmol) in the presence of DIEA (3.86 ml, 22.2 mmol) at room temperature. After 48 hours of agitation the reaction mixture is diluted with ethyl acetate and washed with 1 N soda and then with water. The organic phase is dried on MgSO4, filtered and evaporated to dryness. The syrup obtained is purified by silica column chromatography and eluted with a 97.75/2/0.25 $CH_2Cl_2$/MeOH/$NH_4$OH mixture. Product 1 is isolated in the form of a yellow oil (3.77 g, 95%). This product is taken up with ethyl acetate and salified by addition of a solution of HCl in ether to yield the corresponding hydrochloride in the form of a yellow solid (4.14 g)

$^1$H NMR, DMSO-$d_6$ (ppm): 3.02 (m, 2H); 3.21 (t, 1H); 3.63 (t, 1H); 4.05 (broad s, 2H); 4.34 (s, 2H); 4.52 (t, 2H); 7.32 (m, 3H); 7.43 (m, 2H); 7.53 (m, 1H); 7.66 (m, 2H); 7.92 (d, 1H); 8.00 (m, 1H); 11.49 (s, 1H).

Mass spectrum (ESI+): m/z 359 (M+H$^+$)

Elemental analysis: $C_{20}H_{20}N_2O_1$·HCl and 0.5 $H_2O$

Calculated %: C, 59.41; H, 5.48; N, 6.93

Actual %: C, 59.39; H, 5.56; N, 6.92

EXAMPLES 2 TO 4

Compounds 2 to 4 were synthesized from cinnamic acids and corresponding amines according to the conditions described for the preparation of compound 1.

| Example | R1 | R2 | R3 | Compound name | Mass spectrum (M + H)$^+$ |
|---|---|---|---|---|---|
| 2 | F | H | 4-F | 1-[4-(4-Fluoro-benzyl)-piperazin-1-yl]-3-(2-fluoro-phenyl)-propenone | 343 |
| 3 | Br | H | 4-F | 3-(2-Bromo-phenyl)-1-[4-(4-fluoro-benzyl)-piperazin-1-yl]-propenone | 403 |
| 4 | Cl | H | 4-Me | 3-(2-Chloro-phenyl)-1-[4-(4-methyl-benzyl)-piperazin-1-yl]-propenone | 355 |

EXAMPLE 5

3-(2,6-Difluoro-phenyl)-1-[4-(4-fluoro-benzyl)-piperazin-1-yl]-propenone

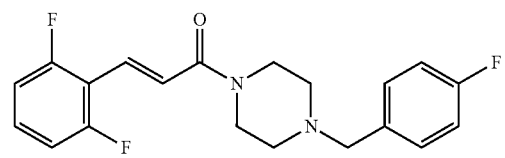 [SMILES: O=C(/C=C/c1c(F)cccc1F)N1CCN(Cc2ccc(F)cc2)CC1]

EXAMPLE 5A

4-[3-(2,6-Difluoro-phenyl)-acryloyl]-piperazine-1-carboxylic acid tert-butyl ester 3-(2,6-Difluoro-phenyl)-acryloyl chloride (3.0 g, 14.8 mmol) in solution in dichloromethane (70 ml) in the presence of PS-DIEA (4.07 g, 13.5 mmol, 3.33 mmol/g) is treated with piperazine-1-carboxylic acid tert-butyl ester (2.3 g, 12.3 mmol) at room temperature. After 6 hours of agitation the reaction mixture is filtered, taken up with dichloromethane and washed with 1 N soda and with water. The organic phase is dried on MgSO$_4$, filtered and evaporated to dryness. The syrup obtained is purified by silica column chromatography and eluted with a 95/4.5/0.5 to 90/9.5/0.5 CH$_2$Cl$_2$/MeOH/NH$_4$OH mixture. Product 5A is isolated in the form of an off-white solid (3.87 g, 89%).

$^1$H NMR, DMSO-d$_6$ (ppm): 1.42 (s, 9H); 3.37 (broad s, 4H); 3.58 (broad s, 4H); 7.22 (m, 2H); 7.50 (m, 1H).

EXAMPLE 5B

-3-(2,6-Difluoro-phenyl)-1-piperazin-1-yl-propenone

4-[3-(2,6-Difluoro-phenyl)-acryloyl]-piperazine-1-carboxylic acid tert-butyl ester (3.87 g, 10.97 mmol) in solution in toluene (50 ml) is treated with trifluoroacetic acid (30 ml, 395 mmol) at room temperature. After 2 hours of agitation the reaction mixture is evaporated to dryness, taken up with dichloromethane and washed with 1 N soda and then with water. The organic phase is dried on MgSO$_4$, filtered and evaporated to dryness. The crude product is isolated for the following reaction (2.3 g, 88%).

EXAMPLE 5

-3-(2,6-Difluoro-phenyl)-1-[4-(4-fluoro-benzyl)-piperazin-1-yl]-propenone

Compound 5B (100 mg, 0.42 mmol) in solution in dichloromethane (5 ml) in the presence of triethylamine (Et$_3$N) (0.088 ml, 0.63 mmol) is treated with 4-fluorobenzyl bromide (0.078 ml, 0.63 mmol) at room temperature. After 15 hours of agitation the reaction mixture is diluted with dichloromethane and washed with water. The organic phase is dried on MgSO$_4$, filtered and evaporated to dryness. The syrup obtained is purified by silica column chromatography and eluted with a 100/0 to 90/10 CH$_2$Cl$_2$/MeOH mixture. Product 5 is isolated in the form of a light-beige solid (72 mg, 48%).

Mass spectrum (ESI+): m/z 361 (M+H$^+$)

EXAMPLES 6 TO 12

Compounds 6 to 12 were synthesized from intermediate 5B and corresponding benzyl chlorides or bromides according to the conditions described for the preparation of compound 5.

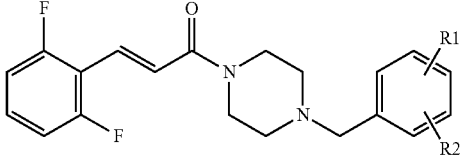

| Example | R1 | R2 | Compound name | Mass spectrum (M + H)$^+$ |
|---|---|---|---|---|
| 6 | 4-Me | H | 3-(2,6-Difluoro-phenyl)-1-[4-(4-methyl-benzyl)-piperazin-1-yl]-propenone | 357 |
| 7 | 3-Me | 4-Me | 3-(2,6-Difluoro-phenyl)-1-[4-(3,4-dimethyl-benzyl)-piperazin-1-yl]-propenone | 371 |
| 8 | 3-F | 4-F | 1-[4-(3,4-Difluoro-benzyl)-piperazin-1-yl]-3-(2,6-difluoro-phenyl)-propenone | 379 |
| 9 | 4-Cl | H | 1-[4-(4-Chloro-benzyl)-piperazin-1-yl]-3-(2,6-difluoro-phenyl)-propenone | 377 |
| 10 | 3-Me | H | 3-(2,6-Difluoro-phenyl)-1-[4-(3-methyl-benzyl)-piperazin-1-yl]-propenone | 357 |
| 11 | 3-Cl | H | 1-[4-(3-Chloro-benzyl)-piperazin-1-yl]-3-(2,6-difluoro-phenyl)-propenone | 377 |
| 12 | 2-Me | H | 3-(2,6-Difluoro-phenyl)-1-[4-(2-methyl-benzyl)-piperazin-1-yl]-propenone | 357 |

EXAMPLES 13 TO 21

EXAMPLE 13A

-3-(2-chloro-phenyl)-1-piperazin-1-yl-propenone

Compound 13A was prepared in two steps from 3-(2-chloro-phenyl)-acryloyl chloride according to the conditions described for the preparation of compound 5B.

EXAMPLES 13 TO 21

Compounds 13 to 21 were synthesized from intermediate 13A according to the conditions described for the preparation of compound 5.

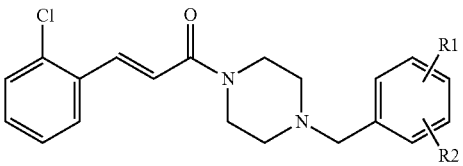

| Example | R1 | R2 | Compound name | Mass spectrum (M + H)$^+$ |
|---|---|---|---|---|
| 13 | 3-Me | H | 3-(2-Chloro-phenyl)-1-[4-(3-methyl-benzyl)-piperazin-1-yl]-propenone | 355 |
| 14 | 4-Cl | H | 1-[4-(4-Chloro-benzyl)-piperazin-1-yl]-3-(2-chloro-phenyl)-propenone | 375 |
| 15 | 2-F | H | 3-(2-Chloro-phenyl)-1-[4-(2-fluoro-benzyl)-piperazin-1-yl]-propenone | 359 |
| 16 | 2-Me | H | 3-(2-Chloro-phenyl)-1-[4-(2-methyl-benzyl)-piperazin-1-yl]-propenone | 355 |
| 17 | 2-Cl | H | 1-[4-(2-Chloro-benzyl)-piperazin-1-yl]-3-(2-chloro-phenyl)-propenone | 375 |
| 18 | 3-F | H | 3-(2-Chloro-phenyl)-1-[4-(3-fluoro-benzyl)-piperazin-1-yl-propenone | 359 |
| 19 | 3-Cl | H | 1-[4-(3-Chloro-benzyl)-piperazin-1-yl]-3-(2-chloro-phenyl)-propenone | 375 |
| 20 | 2-F | 3-F | 3-(2-Chloro-phenyl)-1[4-(2,3-difluoro-benzyl)-piperazin-1-yl]-propenone | 377 |
| 21 | 3-F | 4-F | 3-(2-Chloro-phenyl)-1-[4-(3,4-difluoro-benzyl)-piperazin-1-yl]-propenone | 377 |

EXAMPLE 22

3-(2,6-Difluoro-phenyl)-1-[4-(2-fluoro-benzyl)-piperazin-1-yl]-propenone

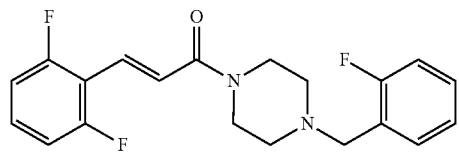 [SMILES: O=C(/C=C/c1c(F)cccc1F)N1CCN(Cc2ccccc2F)CC1]

A mixture of intermediate 5B (60 mg, 0.25 mmol) and 2-fluoro-benzaldehyde (0.031 ml, 0.3 mmol) in solution in dichloromethane (3 ml) in the presence of acetic acid (0.057 ml, 1.0 mmol) is treated with MP-BH$_3$CN (117 mg, 0.275 mmol, 2.35 mmol/g) at room temperature. After 24 hours of agitation the reaction mixture is filtered on a ChemElut cartridge previously impregnated with 1 N NaOH and then evaporated to dryness. The syrup obtained is purified by silica column chromatography and eluted with a 100/0 to 95/5 CH$_2$Cl$_2$/MeOH mixture. Product 22 is isolated in the form of a yellow syrup (23 mg, 25%).

Mass spectrum (ESI+): m/z 361 (M+H$^+$)

EXAMPLE 23

1-[4-(2-Fluoro-benzyl)-piperazin-1-yl]-3-(2-nitrophenyl)-propenone

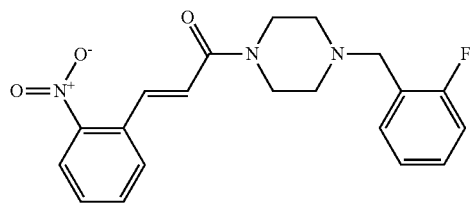 [SMILES: O=C(/C=C/c1ccccc1[N+](=O)[O-])N1CCN(Cc2ccccc2F)CC1]

EXAMPLE 23A 3-(2-Nitro-phenyl)-1-piperazin-1-yl-propenone

Compound 23A was prepared in two steps from 3-(2-nitrophenyl)-acryloyl chloride according to the conditions described for the preparation of compound 5B.

EXAMPLE 23

1-[4-(2-Fluoro-benzyl)-piperazin-1-yl]-3(2-nitrophenyl)-propenone

Compound 23 was synthesized from compound 23A according to the conditions described for the preparation of compound 22.

Mass spectrum (ESI+): m/z 370 (M+H$^+$)

EXAMPLE 24

1-(4-Cyclohexylmethyl-piperazine-1-yl)-3-(2,6-difluoro-phenyl)-propenone

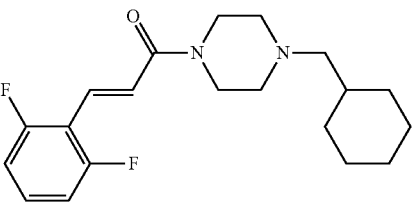 [SMILES: O=C(/C=C/c1c(F)cccc1F)N1CCN(CC2CCCCC2)CC1]

Compound 24 was synthesized from compound 5B according to the conditions described for the preparation of compound 22.

Mass spectrum (ESI+): m/z 349 (M+H$^+$)

EXAMPLES 25 TO 28

Compounds 25 to 28 were synthesized from 1-cyclohexylmethyl-piperazine and corresponding cinnamic acids according to the conditions described for the preparation of compound 1.

| Example | R1 | R2 | Compound name | Mass spectrum (M + H)$^+$ |
|---|---|---|---|---|
| 25 | NO$_2$ | H | 1-(4-Cyclohexylmethyl-piperazin-1-yl)-3-(2-nitro-phenyl)-propenone | 358 |
| 26 | CN | H | 2-[3-(4-Cyclohexylmethyl-piperazin-1-yl)-3-oxo-propenyl]-benzonitrile | 338 |
| 27 | F | H | 1-(4-Cyclohexylmethyl-piperazin-1-yl)-3-(2-fluoro-phenyl)-propenone | 331 |
| 28 | Cl | H | 3-(2-Chloro-phenyl)-1-(4-cyclohexylmethyl-piperazin-1-yl)- | 347 |

EXAMPLES 29 TO 33

Compounds 29 to 33 were synthesized from compound 23A and corresponding benzyl chlorides or bromides according to the conditions described for the preparation of compound 5.

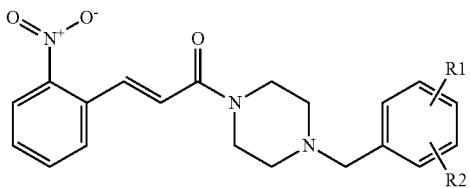

| Example | R1 | R2 | Compound name | Mass spectrum (M + H)+ |
|---|---|---|---|---|
| 29 | 4-F | H | 1-[4-(4-Fluoro-benzyl)-piperazin-1-yl]-3-(2-nitro-phenyl)-propenone | 370 |
| 30 | 4-Me | H | 1-[4-(4-Methyl-benzyl)-piperazin-1-yl]-3-(2-nitro-phenyl)-propenone | 366 |
| 31 | 3-F | 4-F | 1-[4-(3,4-Difluoro-benzyl)-piperazin-1-yl]-3-(2-nitro-phenyl)-propenone | 388 |
| 32 | 4-Cl | H | 1-[4-(4-Chloro-benzyl)-piperazin-1-yl]-3-(2-nitro-phenyl)-propenone | 386 |
| 33 | 3-Me | H | 1-[4-(3-Methyl-benzyl)-piperazin-1-yl]-3-(2-nitro-phenyl)-propenone | 366 |

EXAMPLE 34

1-[4-(2,6-Dimethyl-benzyl)-piperazin-1-yl]-3-(2-nitro-phenyl)-propenone

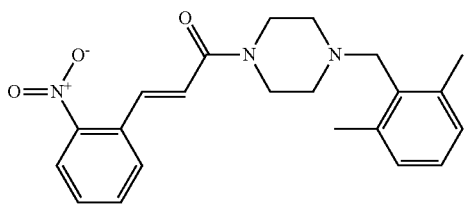 [SMILES: Cc1cccc(C)c1CN1CCN(C(=O)/C=C/c2ccccc2[N+](=O)[O-])CC1]

A mixture of compound 23A (70 mg, 0.27 mmol) and 2,5-dimethyl-benzaldehyde (40 mg, 0.32 mmol) in solution in dichloroethane (3 ml) in the presence of acetic acid (0.092 ml, 1.6 mmol) is treated with NaBH(OAc)$_3$ (63 mg, 0.297 mmol) at room temperature. After 24 hours of agitation the reaction mixture is treated with saturated NaHCO$_3$ (2 ml), filtered on a ChemElut cartridge and evaporated to dryness. The syrup obtained is purified by silica column chromatography and eluted with a 100/0 to 90/10 CH$_2$Cl$_2$/MeOH (+10% NH$_4$OH) mixture. Product 34 is isolated and then salified by the addition of HCl in ether to yield a white solid (40 mg, 40%).

Mass spectrum (ESI+): m/z 380 (M+H$^+$)

EXAMPLES 35 TO 38

Compounds 35 to 38 were synthesized from compounds 5B, 13A and 23A and corresponding phenethyl chlorides or bromides according to the conditions described for the preparation of compound 5.

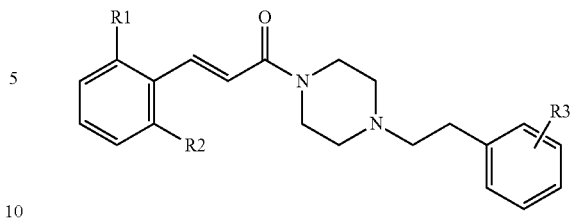

| Example | R1 | R2 | R3 | Compound name | Mass spectrum (M + H)+ |
|---|---|---|---|---|---|
| 35 | F | F | H | 3-(2,6-Difluoro-phenyl)-1-(4-phenethyl-piperazin-1-yl)-propenone | 357 |
| 36 | NO$_2$ | H | H | 3-(2-Nitro-phenyl)-1-(4-phenethyl-piperazin-1-yl)-propenone | 366 |
| 37 | Cl | H | H | 3-(2-Chloro-phenyl)-1-(4-phenethyl-piperazin-1-yl)-propenone | 355 |
| 38 | Cl | H | 4-F | 3-(2-Chloro-phenyl)-1-{4-[2-(4-fluoro-phenyl)-ethyl]-piperazin-1-yl}-propenone | 373 |

The derivatives of the present invention are PAR-1 receptor antagonists as the results of the models described below demonstrate:

In a variety of cell types, activation of PAR-1 receptors by the SFLLR peptide (a selective PAR-1 agonist) triggers an intracellular signal cascade leading to the release of calcium by the endoplasmic reticulum. Chinese hamster ovarian (CHO) cells constituently express PAR-1 receptor. In this cell line, the release of calcium consecutive to receptor activation by SFLLR is measured by a fluorometry technique (fluorometric imaging plate reader, or FLIPR) using a selective probe for calcium (Fluo-3AM). The emission of fluorescence is pharmacologically proportional to the efficiency of the PAR-1 agonist and to its concentration. The compounds described in the present invention have demonstrated that they are capable of antagonizing PAR-1 receptors and thus decreasing the release of calcium induced by the agonist.

Materials:

Culture medium: Ham's F-12 (Ham, R. G., Proc. Nat. Acad. Sci. 1965, 53: 288) supplemented with 10% fetal calf serum and antibiotic (Probenicid, 2.5 mM).

Fluorescent probe: Fluo-3AM (4 μM; Teflabs, Austin, Tex., USA)

Agonist: SFLLR-NH$_2$ (Serine, phenylalanine, leucine, leucine, arginine).

Methods: CHO cells are inoculated in 96-well plates (60,000 cells per well) in the presence of 200 μl of culture medium for 24 hours. The cells are incubated with the calcium fluorescent probe for 1 hour at 37° C. The cells are then washed 10 minutes before the signal is measured. PAR-1 antagonist is then injected (0.01 μM to 10 μM). The plates are placed in the FLIPR (Molecular Devices, UK) to measure calcium fluorescence at two wavelengths (488 nm and 540 nm: Sullivan et al., Calcium Signaling Protocols 1999, 125-136). Measurements are taken for 5 min before the antagonist is added and for 10 min following its administration. Maximum fluorescence minus baseline fluorescence is measured in 4 different wells. The test is carried out in duplicate. Under these conditions, the derivatives of the present invention were identified as PAR-1 receptor antagonists (antagonism>60% of the calcium signal at 10 μM). The dose-response curves (0.01 μM to 32 μM) obtained with the SFLLR agonist allowed determination of the effective concentration inducing 50% of the maximum effect (EC$_{50}$). The strengths (pA2) of some of the PAR-1 antagonists described in the present invention were calculated using the method of Arunlakshana and Schild (Brit. J. Pharmacol., 1959, 14: 48-58) from the $EC_{50}$ shifts observed at three concentrations.

Results:

The several examples which follow, chosen among the compounds of the present invention, illustrate the completely unexpected capacity of these compounds to antagonize PAR-1 receptors.

| Examples | pA2 |
|---|---|
| 1 | 6.42 |
| 2 | 6.50 |
| 3 | 6.36 |
| 4 | 6.05 |
| 8 | 6.32 |
| 10 | 6.46 |
| 15 | 6.39 |
| 25 | 6.78 |
| 28 | 6.12 |
| 29 | 6.98 |

The in vivo antiplatelet aggregation and antithrombotic activities of PAR-1 antagonists have been shown in a guinea pig model of arterial thrombosis, which has very high hemodynamic shear stress. In a vascular bed, an endothelial lesion causes the intravascular formation of a platelet-rich thrombus that will gradually occlude all of the vessel's lumen. The platelet aggregation process is strongly activated by thrombin via PAR-1 receptors. The compounds described in the present invention have demonstrated that they are capable of antagonizing PAR-1 receptors and thus delaying thrombus formation.

Materials:

The studies are conducted using guinea pigs (PAR-1 receptors similar to man). Irradiation by means of a green laser light in the presence of a photosensitizing agent (Rose Bengal administered intravenously) damages the carotid endothelium. The carotid flow rate is quantified using a Transonic flow probe. The time required to completely occlude the carotid (flow rate of 0) is measured.

Methods:

After the animal is anesthetized (60 mg/kg pentobarbital), 5 mm of the carotid artery is resected and the laser is placed 4 mm above the artery. A flow probe placed upstream measures occlusion time. Rose Bengal (20 mg/kg) is administered by intravenous route and the vessel is irradiated at a wavelength of 514 nm (for 3 min). PAR-1 antagonists are administered by intravenous route using a bolus (over 2 min immediately before administration of Rose Bengal) followed by a 15-minute perfusion which begins when the laser is turned on.

Results:

Certain compounds described in the present invention have shown that they are able, after administration by intravenous route at doses from 0.16 mg/kg to 2.5 mg/kg, to delay the time before the formation of a thrombus from 5% to 135% compared to animals receiving vehicle alone.

The derivatives according to the invention are also of use in the treatment of atrial fibrillation.

In the case of postinfarction cardiac-cavity volume overload, the right and left auricles dilate, thus constituting the substrate for the genesis of atrial fibrillation. The disturbance of hemostasis in the cavity of the dilated auricle of a patient suffering from atrial fibrillation leads to an abnormal concentration of thrombin. The inventors have demonstrated that this accumulation of thrombin is responsible for an up-regulation of PAR-1 which can trigger the proliferation of fibroblasts as well as the formation of platelet thrombus.

By their mechanism of action, PAR-1 antagonists can thus prevent atrial dilation, fibroblast proliferation and thrombus formation in the auricle of a patient suffering from atrial fibrillation.

As a result, a PAR-1 antagonist constitutes an effective preventative and/or curative treatment for atrial fibrillation. The compounds described in the present invention have demonstrated that they are capable of antagonizing PAR-1 receptors and preventing auricle dilation.

Materials:

The studies are carried out using male rats. Because they tolerate surgery best, rats in a weight range of 180-200 g on arrival were chosen for the experiment. Measurements of the various myocardial cavities are conducted by echocardiography on the anesthetized animal.

Methods:

The animal is anesthetized by a 3.5% mixture of isoflurane in oxygen (Aerrane, Baxter Laboratories). A thoracotomy perpendicular to the sternum of approximately 2 cm is performed at the level of the fourth intercostal space towards the left forefoot. A ligature (4-0 silk, CC1 needle, Ethicon) is passed around the left coronary artery 1 mm from its origin. A surgical knot, sufficiently tight to completely occlude the vessel, is tied around the left coronary artery. The continuously-recording electrocardiogram makes it possible to verify the satisfactory positioning of the ligature. Two months after the procedure, the animals are again anesthetized for an echocardiographic measurement of the cardiac cavities and a measurement of blood velocity within the myocardium using pulsed Doppler. Lastly, the animals are euthanized by sodium pentobarbital overdose (160 mg/kg, IP) for various histological measurements. The animals are force-fed daily PAR-1 antagonist products from 24 h after infarction until the animal is sacrificed.

Results:

Certain compounds described in the present invention have shown that they are able, after administration by oral route in doses from 10-100 mg/kg/d for 60 days, to reduce by 20% to 90% the auricle surface (measured by echocardiography) compared to untreated animals.

The present invention also relates to pharmaceutical compositions containing as an active ingredient a compound of general formula (I), or a pharmaceutically-acceptable salt thereof, mixed or combined with a suitable excipient. Such compositions can assume the form, for example, of solid or liquid compositions, emulsions, lotions or creams.

As solid compositions for oral administration, tablets, pills, powders (in gelatin capsules or in packets) or granules can be used. In such compositions, the active ingredient according to the invention is mixed with one or more inert diluents, such as starch, cellulose, sucrose, lactose or silica, under an argon flow. Such compositions may also include substances other than diluents, for example one or more lubricants such as magnesium stearate or talc, a colorant, a coating (for sugar-coated pills) or a varnish.

As liquid compositions for oral administration, the following can be used: pharmaceutically-acceptable solutions, suspensions, emulsions, syrups and elixirs containing inert diluents such as water, ethanol, glycerol, vegetable oils or liquid paraffin. Such compositions can include substances other than diluents, for example wetting, sweetening, thickening, flavoring or stabilizing agents.

Sterile compositions for parenteral administration can be, preferably, aqueous or non-aqueous solutions, suspensions or emulsions. As a solvent or vehicle, the following can be used:

water, propylene glycol, polyethylene glycol, vegetable oils, in particular olive oil, injectable organic esters, for example ethyl oleate or other suitable organic solvents. Such compositions can also contain additives, in particular wetting agents, isotonic agents, emulsifiers, dispersants and stabilizers. Sterilization can be achieved in several ways, for example by sterilizing filtration, by incorporating sterilizing agents in the composition, by irradiation or by heating. Such compositions can also be prepared in the form of sterile solid compositions that can be dissolved in sterile water or in any other injectable sterile medium just before use.

Compositions for rectal administration are suppositories or rectal capsules that contain, in addition to the active product, excipients such as cocoa butter, semi-synthetic glycerides or polyethylene glycols.

Compositions for topical administration can be creams, lotions, eye drops, mouth washes, nose drops or aerosols, for example.

Doses depend on desired effect, treatment duration and administration route, and are generally between 0.001 g and 1 g (preferably between 0.005 g and 0.75 g) per day, preferably by oral route for an adult, with unit doses ranging from 0.1 mg to 500 mg of active substance.

Generally, the doctor will establish suitable dosing according to the patient's age, weight and other specific factors of the case.

According to a specific embodiment, the present invention also relates to products containing a compound according to general formula (I) and another cardiovascular agent as a combination product for simultaneous, separate or time-release use in cardiovascular therapy, the other cardiovascular agent able to be an antiplatelet agent such as aspirin, clopidogrel, ticlopidine, abciximab, tirofiban or eptifibatide.

According to additional characteristics of the present invention, compounds of general formula (I) are of use in the manufacture of a drug to inhibit the proliferation of smooth muscle cells (restenosis) and/or for the curative and/or preventive treatment of the proliferation of endothelial, fibroblast, cardiofibroblast, glial, smooth muscle or cancer cells.

The invention claimed is:

1. Compounds of general formula (I):

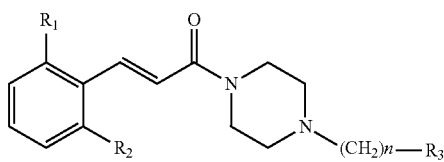

wherein $R_1$ is cyano, $R_2$ is hydrogen, n equals 1, and $R_3$ is phenyl substituted by one or more halogens or $C_1$-$C_6$ alkyls, and therapeutically-acceptable salts thereof.

2. Compounds of general formula (I):

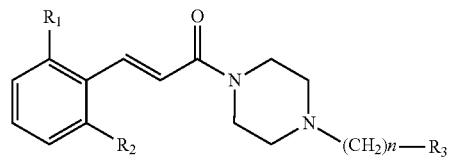

wherein $R_1$ is halogen, $R_2$ is hydrogen, n equals 1, and $R_3$ is cyclohexyl, and therapeutically-acceptable salts thereof.

3. Compounds of general formula (I):

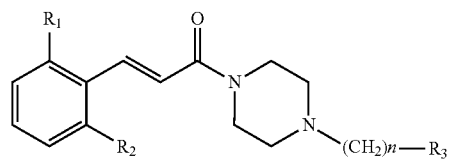

wherein $R_1$ is cyano, $R_2$ is hydrogen, n equals 1, and $R_3$ is cyclohexyl, and therapeutically-acceptable salts thereof.

4. Pharmaceutical compositions containing as an active ingredient at least one compound according to any one of claims 1, 2, or 3, in combination with a pharmaceutically—acceptable vehicle.

* * * * *